(12) United States Patent
Bacchi

(10) Patent No.: US 7,838,680 B2
(45) Date of Patent: Nov. 23, 2010

(54) PROCESS FOR PREPARING HETEROCYCLIC DERIVATIVES

(75) Inventor: Sergio Bacchi, Verona (IT)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 12/608,184

(22) Filed: Oct. 29, 2009

(65) Prior Publication Data

US 2010/0048895 A1 Feb. 25, 2010

Related U.S. Application Data

(63) Continuation of application No. 11/693,757, filed on Mar. 30, 2007, now abandoned.

(30) Foreign Application Priority Data

Apr. 3, 2006 (GB) ................................. 0607899.2

(51) Int. Cl.
*C07D 417/02* (2006.01)
(52) U.S. Cl. ..................... 548/136; 548/263.2
(58) Field of Classification Search ........................ None
See application file for complete search history.

(56) References Cited

U.S. PATENT DOCUMENTS

2002/0032238 A1 3/2002 Priepke et al.

FOREIGN PATENT DOCUMENTS

WO WO-2005/080382 A * 9/2005
WO WO 2007/022980 3/2007

OTHER PUBLICATIONS

Kane, et al.: 2,4-Dihydro-3*H*-1,2,4-triazole-3-thiones as Potential Antidepressant Agents, J Med Chem, 1988, 31, 1253-1258.
A. Shafiee, et al., Syntheses of Substituted-oxazolo-1,3,4-thiadiazoles, 1,3,4-Oxadiazoles, and 1,2,4-Triazoles, J. Heterocyclic Chem, 32, 1235 (1995).
E.B. Vasil'eva, et al. Synthesis of Trifluoroalkyl- and Fluoroaryl-Substituted 4,5-Dihydro-1*H*-1,2,4-triazole-5-thiones, Russian Journal of Organic Chemistry, 40, 6, 2004, 874-878.
Ech-Chahad, A. Minassi, A. Berton L, Appendino G; An expeditious hydroxyamidation of carboxylic acids; Tetrahedron Letters; Jan. 8, 2005; vol. 46 No. 31; 5113-5115; Elsevier; Amsterdam NL.

* cited by examiner

*Primary Examiner*—Kamal A Saeed
(74) *Attorney, Agent, or Firm*—James M. Kanagy; Edward R. Gimmi; Charles M. Kinzig

(57) ABSTRACT

The present invention relates to a novel process, useful for preparing key intermediates of formula (I) in the synthesis of various compounds, among them compounds which are potent and specific antagonists of D3 receptors,

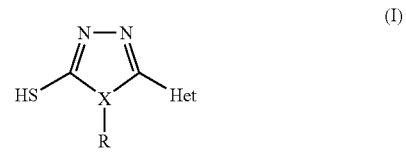

(I)

in which
X may be Nitrogen or Sulfur;
Het means aryl or heteroaryl; each of which may be substituted by 1 to 4 groups J selected from:
halogen, C1-C6 alkyl C1-C6 alkoxy, halo C1-C6 alkyl C2-C6 alkenyl,
C2-C6 alkynyl, halo C1-C6 alkoxy, —C(O)R$_1$, nitro, hydroxy, —NR$_2$R$_3$, cyano or a group Z;
R$_1$ is a C1-C4 alkyl —OR$_3$ or —NR$_3$R$_4$;
R$_2$ is hydrogen or C1-C6 alkyl;
R$_3$ is hydrogen or C1-C6 alkyl;
R is H, C1-C6 alkyl aryl, benzyl; each of which may be substituted by 1 to 4 groups J;
according to the following Scheme 1:

Scheme 1

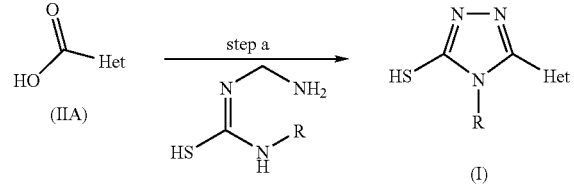

in which
step a means a reaction in basic conditions of compounds (IIA) with 3-thiosemicarbazide derivatives, followed by a treatment with an inorganic base and n-propane phosphonic cyclic anhydride and final pH adjustment with inorganic acids to give compounds of formula (II).

6 Claims, No Drawings

PROCESS FOR PREPARING HETEROCYCLIC DERIVATIVES

This application is a continuation of application Ser. No. 11/693,757 filed 30 Mar. 2007 now abandoned which claims benefit to GB 0607899.2 filed 3 Apr. 2006.

The present invention relates to a novel process, useful for preparing key intermediates in the synthesis of various compounds, among them compounds which are potent and specific antagonists of D3 receptors.

The present invention relates to a novel process for preparing thiazole or triazole derivatives of formula (I)

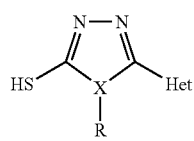

in which
X may be Nitrogen or Sulfur;
Het means aryl or heteroaryl; each of which may be substituted by 1 to 4 groups J selected from:
halogen, C1-C6 alkyl C1-C6 alkoxy, halo C1-C6 alkyl C2-C6 alkenyl, C2-C6 alkynyl, halo C1-C6 alkoxy, —C(O)R$_1$, nitro, hydroxy, —NR$_2$R$_3$, cyano or a group Z;
R1 is a C1-C4 alkyl —OR3 or —NR3R$_4$;
R$_2$ is hydrogen or C1-C6 alkyl;
R$_3$ is hydrogen or C1-C6 alkyl;
R is H, C1-C6 alkyl aryl, benzyl; each of which may be substituted by 1 to 4 groups J;
according to the following Scheme 1:

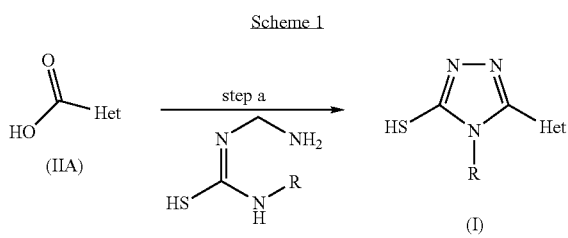

in which
step a means a reaction in basic conditions of compounds (IIA) with 3-thiosemicarbazide derivatives, followed by a treatment with an inorganic base and n-propane phosphonic cyclic anhydride and final pH adjustment with inorganic acids to give compounds of formula(I).

The term C1-C6 alkyl as used herein as a group or a part of the group refers to a linear or branched alkyl group containing from 1 to 6 carbon atoms; examples of such groups include methyl, ethyl, propyl, isopropyl, n-butyl, isobutyl, tert butyl, pentyl or hexyl.

The term halogen refers to a fluorine, chlorine, bromine or iodine atom.

The term halo C1-C6 alkyl, means an alkyl group having one or more carbon atoms and wherein at least one hydrogen atom is replaced with halogen such as for example a trifluoromethyl group and the like.

The term C1-C6 thioalkyl may be a linear or a branched chain thioalkyl group, for example thiomethyl, thioethyl, thiopropyl, thioisopropyl, thiobutyl, thiosec-butyl, thiotert-butyl and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a linear or a branched chain alkoxy group, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as OCHF$_2$, or OCF$_3$.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term aryl means an aromatic carbocyclic moiety such as phenyl, biphenyl or naphthyl.

The term heteroaryl means an aromatic heterocycle ring of 5 to 10 members and having at least one heteroatom selected from nitrogen, oxygen and sulfur, and containing at least 1 carbon atom, including both mono- and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, triazolyl, tetrazolyl, quinazolinyl, and benzodioxolyl.

The term 5-6 membered heterocycle means, according to the above definition, a 5-6 monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles include heteroaryls as defined above. The heterocycle may be attached via any heteroatom or carbon atom. Thus, the term includes (but is not limited to) morpholinyl, pyridinyl, pyrazinyl, pyrazolyl, thiazolyl, triazolyl, imidazolyl, oxadiazolyl, oxazolyl, isoxazolyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like.

Compounds of formula (II) can be useful, but are not limited to, for the preparation of D3 antagonists of formula (IA), as disclosed in WO2005/080382:

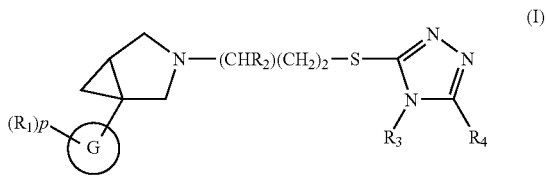

wherein
- G is selected from a group consisting of: phenyl, pyridyl, benzothiazolyl, indazolyl;
- p is an integer ranging from 0 to 5;
- $R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
- $R_2$ is hydrogen or $C_{1-4}$alkyl;
- $R_3$ is $C_{1-4}$alkyl;
- $R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
- $R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

The preparation of compounds of formula (II) described in WO2005/080382 employed 1-hydroxybenzotriazole (HOBt) together with 1,3-dicyclohexylcarbodiimide (DCC).

The disadvantages of this reagents at an industrial level may be summarised as follows: HOBt and its by-products have an explosive nature and DCC and its by-product are always difficult to fully remove.

The process solves the above problems by using n-propane phosphonic cyclic anhydride, T3P, as condensation agent.

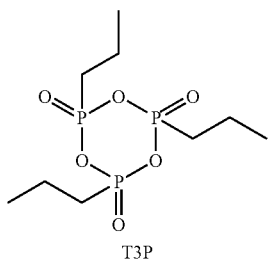

T3P

The T3P was first used in the petide synthesis in 1980 by H. Wissmann (Angew. Chem., 1980, 92, 129) and is steadily gaining importance in organic synthesis because is less toxic and safer compared to other common condensation agents, such as DCC.

The reagent does not afford any water insoluble by-product. T3P is used as 50% solution in ethyl acetate in the process of the present invention and does not need the isolation of the intermediate hydrazine-carbothiamide. Similarly, T3P is available as 50% solution in DMF (dimethylformamide) and may be employed in the process of the present invention.

The process of the present invention can be depicted in more details as follows:

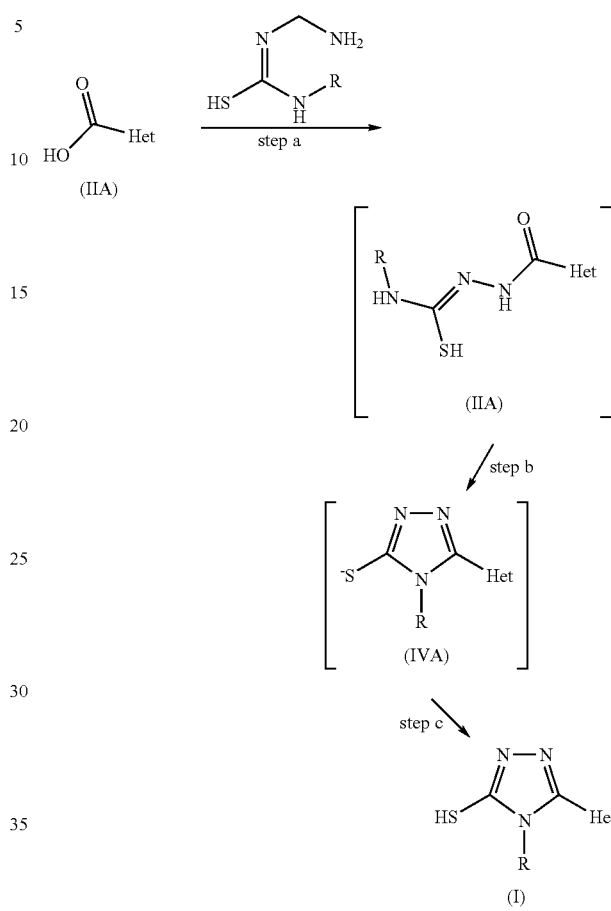

The starting material, the heterocyclic carboxylic acid, generally commercially available or which may be prepared according to known methods in the literature, in an amount of 1 equivalent may be conveniently dissolved in the appropriate solvent (for example dimethylformamdide; ethyl acetate; acetonitrile and tetrahydrofurane and other polar aprotic solvent) and treated with a slightly excess of derivatives of 3-thiosemicarbazide (1.10 eq)., such as 4-methyl derivative. Then an organic base (e.g. triethylamine, diisopropylethylamine and possibly other aliphatic of aromatic amines) is added at RT.

N-propane phosphonic cyclic anhydride (50% w/w in ethyl acetate) may be then added at a temperature ranging from 0 to 40 degrees dropwise. In case the addition is made at about 0° C., the temperature is then maintained below 15° C. over 20-60 minutes. The resulting mixture was then stirred at 20° C. for 2-16 hours.

The mixture is then diluted with an aqueous solution of an appropriate inorganic base until basic pH was reached. The suitable base may be selected among: potassium carbonate, sodium carbonate, sodium hydroxide, potassium hydroxide.

The resulting bi-phasic mixture (when observed) is then allowed separating and the upper organic layer discarded. The aqueous layer is then heated to 50-90° C. (internal temperature) for half an hour to several hours until reaction completion.

After cooling down to 20° C., an appropriate mineral acid, (e.g HCl 37%) is then slowly added to adjust the pH as needed. (4 to 8).

The suspension is then generally stirred for 2-16 hours, then the solid was filtered, washed with pure water and dried in a vacuum oven at 40-60° C. until dryness. The final product is isolated from the aqueous mixture uncontaminated by phosphorous derivatives.

EXAMPLES

In the Examples unless otherwise stated:

All temperatures refers to ° C. Infrared spectra were measured on a FT-IR instrument. Compounds were analysed by direct infusion of the sample dissolved in acetonitrile into a mass spectra operated in positive electro spray (ES$^+$) ionisation mode. Proton Magnetic Resonance ($^1$H-NMR) spectra were recorded at 400 MHz, chemical shifts are reported in ppm downfield (d) from Me$_4$Si, used as internal standard, and are assigned as singlets (s), broad singlets (bs), doublets (d), doublets of doublets (dd), triplets (t), quartets (q) or multiplets (m). Column chromathography was carried out over silica gel (Merck AG Darmstaadt, Germany). The following abbreviations are used in the text: T3P=N-propane Phosphonic Cyclic Anhydride, EtOAc=ethyl acetate, DIPEA=N,N-diisopropylethylamine.

| | |
|---|---|
| Column | Phenomenex LUNA |
| Detector | UV |
| Wavelength | 220 nm |
| Flow | 1 mL/min |
| Injection volume | 1 μL |
| Temperature | 40° C. |
| Run Time | 8 min |
| Mobile Phase | A: 0.05% v/v TFA in water/B: 0.05% v/v TFA in acetonitrile |
| Gradient | FAST gradient: Step 1: Time-Reserv.A-Reserv.B Time 0 min 100% A Step 2: Time-Reserv.A-Reserv.B Time 8 min 5% A Step 3: Time-Reserv.A-Reserv.B Time 8.01 min 100% A |

Example 1

Preparation of 4-Methyl-5-(4-methyl-1,3-oxazol-5-yl)-2,4-dihydro-3H-1,2,4-triazole-3-thione

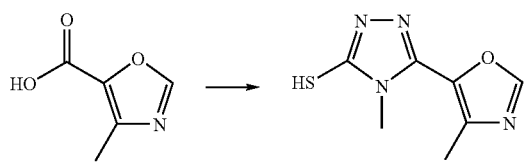

4-Methyl-1,3-oxazole-5-carboxylic acid (commercially available) (12.9 g, 101.5 mmol) was dissolved in DMF (60 mL) and treated with 4-methyl-3-thiosemicarbazide (11.61 g, 1.10 eq). Then DIPEA (31.0 mL, 1.75 eq) was added at 20° C. Under ice bath cooling, T3P 50% w/w in EtOAc (90 mL) was added dropwise, maintaining the temperature below 15° C. over 20 minutes. The resulting mixture was then stirred at 20° C. for 6 hours.

The mixture was diluted with NaOH 4 M (120.0 mL). The resulting bi-phasic mixture was allowed separating and the upper organic layer discarded. The aqueous layer (pH=8) was adjusted to pH=11 with additional NaOH 4 M (60 mL) and then heated to 70° C. (internal temperature) for 30 min. After cooling down over night, HCl 37% was slowly added until pH=5 was reached.

The suspension was stirred for 8 hours, then the solid was filtered and washed with water (60 mL), and it was dried in a vacuum oven at 40° C. overnight.

Yield: 10.48 g, 53.4 mmol, 53% th
$^1$H NMR (DMSO-d6, 600 MHz, δ ppm): 14.11 (bs, 1H), 8.60 (s, 1H), 3.61 (s, 3H), 2.33 (s, 3H)
MH$^+$=197

Example 2

Preparation of 5-(2,4-dimethyl-1,3-thiazol-5-yl)-4-methyl-2,4-dihydro-3H-1,2,4-triazole-3-thione

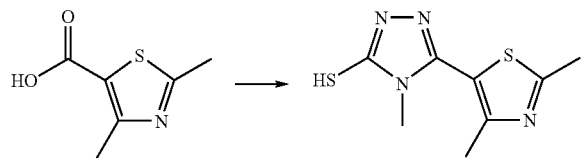

2,4-Dimethyl-1,3-oxazole-5-carboxylic acid (commercially available) (5 g, 31.8 mmol) and 4-methyl-3-thiosemicarbazide (3.68 g, 1.10 eq) were dissolved in DMF (15 mL). Then DIPEA (10.0 mL, 1.80 eq) was added at 20° C. Under ice bath cooling, T3P 50% w/w in EtOAc (35 mL, 1.50 eq) was added dropwise, maintaining the temperature below 10° C. The resulting mixture was then stirred at 20° C. for 2 h.

The mixture was diluted with water (20 mL), then NaOH 4 M was added (20.0 mL). The organic phase was discarded and the acqueous phase was heated to 70° C. (internal temperature) for 90 min. After cooling down to 50° C., HCl 37% was slowly added until pH=6.5 was reached.

The suspension was cooled to 5° C. and the solid was filtered and washed with water, and it was then dried in a vacuum oven at 40° C. overnight.

Yield: 5.45 g, 24.4 mmol, 77% th
$^1$H NMR (DMSO-d6, 400 MHz, δ ppm): 14.02 (bs, 1H), 3.39 (s, 3H), 2.69 (s, 3H), 2.34 (s, 3H)
MH$^+$=227

Example 3

Preparation of 4-methyl-5-(2-methyl-3-pyridinyl)-2,4-dihydro-3H-1,2,4-triazole-3-thione

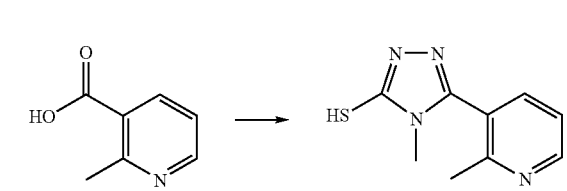

2-Methylnicotinic acid (commercially available) (5 g, 36.5 mmol) and 4-methyl-3-thiosemicarbazide (4.22 g, 1.10 eq) were dissolved in EtOAc (15 mL). Then DIPEA (14.5 mL, 2.28 eq) was added at 20° C. Under ice bath cooling, T3P 50% w/w in EtOAc (32.5 mL, 1.50 eq) was added drop wise, maintaining the temperature below 15° C. The resulting mixture was then stirred at 20° C. for 90 min. The mixture was diluted with water (10 mL), then NaOH 4 M was added (18.5 mL). The organic layer was discarded and the remaining aqueous layer was heated to 70° C. (internal temperature) for 2 h 45 min. After cooling down to ambient temperature, a suspension was obtained, which had a pH of about 7.5 to 8.0.

HCl 37% was slowly added until pH=5 was reached.

The solid was filtered and it was then dried in a vacuum oven at 40° C. overnight.

Yield: 7.04 g, 34.1 mmol, 93% th $^1$H NMR (DMSO-d6, 600 MHz, δ ppm): 14.01 (bs, 1H), 8.66 (dd, 1H), 7.96 (dd, 1H), 7.42 (dd, 1H), 3.29 (s, 3H), 2.42 (s, 3H)

MH$^+$=207

Example 4

Preparation of 4-methyl-5-(4-pyridazinyl)-2,4-dihydro-3H-1,2,4-triazole-3-thione

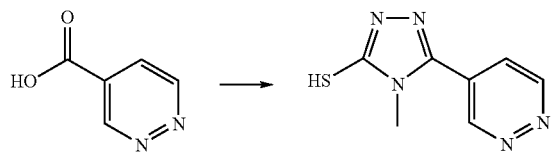

4-Pyridazinecarboxylic acid (commercially available) (5 g, 40.3 mmol) and 4-methyl-3-thiosemicarbazide (4.66 g, 1.10 eq) were dissolved in DMF (15 mL). Then DIPEA (12.5 mL, 1.78 eq) was added at 20° C. Under ice bath cooling, T3P 50% w/w in EtOAc (36 mL, 1.50 eq) was added dropwise, maintaining the temperature below 20° C. The resulting mixture was then stirred at 20° C. for 30 min. HPLC showed a new peak at 0.6 minutes and at 2.93 min.

The mixture was diluted with water (20 mL), then NaOH 4 M was added (20.0 mL). The organic layer was discarted and the remaining aqueous phase was heated to 70° C. (internal temperature) for 5 h, until, by HPLC, complete conversion was observed. After cooling down to ambient temperature, a suspension was obtained, which had a pH of about 7.5 to 8.0. HCl 37% was slowly added until pH=5 was reached.

The solid was filtered and washed with water (3 times with 20 mL), and it was then dried in a vacuum oven at 40° C. overnight.

Yield: 6.37 g, 33.0 mmol, 82% th $^1$H NMR (DMSO-d6, 500 MHz, δ ppm): 14.29 (bs, 1H), 9.58 (d, 1H), 9.47 (d, 1H), 8.09 (d, 1H), 3.64 (s, 3H)

MH$^+$=194

Example 5

Preparation of 5-(2,4-dimethyl-1,3-oxazol-5-yl)-4-methyl-2,4-dihydro-3H-1,2,4-triazole-3-thione

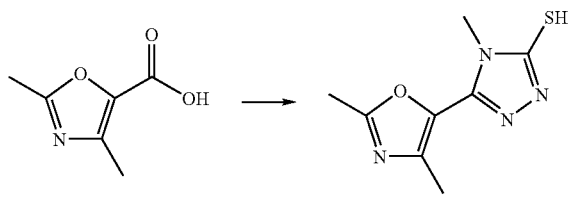

4-methyl-3-thiosemicarbazide (4.5 g, 42.8 mmol) was dissolved in DMF (12.5 mL, 2.5 vol) under stirring. Commercially available 2,4-dimethyl-1,3-oxazole-5-carboxylic acid (5 g, 35.4 mmol) and DIPEA-diisopropylethylamine-(15.5 mL, 89 mmol) were added. Mixture was cooled down to 5° C. with an ice-water bath and a solution of T3P 50% w/w in ethyl acetate (45.5 mL, 76.4 mmol) was added drop wise in 15 minutes maintaining temperature below 10° C. At the end of the addition, mixture was allowed to reach ambient temperature and stirred for 2 hours under nitrogen. The mixture was diluted with 22.5 mL of water and 22.5 mL of a solution of NaOH 32% w/w under stirring (final pH=12). After separation, the upper organic layer was discarded while the water phase was heated to 70° C. (65° C. internal). The pH of the mixture was checked over time and pH adjusted to 12 if necessary. The heating was kept for a total amount of 3 hours.

After cooling down to ambient temperature, 2.5 mL of a solution of HCl 37% w/w were added until pH was 8. A solid started precipitating and the suspension was stirred over night.

The mixture was filtered, the cake washed with 22.5 mL of water and the collected solid dried under vacuum oven at 40° C. for 5 hours.

Yield 4.28 g; 57% theoretical

1H-NMR

600 MHz, DMSO-d6: 2.26 (3H, s), 2.48 (3H, s), 3.59 (3H, s), 14.07 (1H, br. s.)

MH$^+$ [211]

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A process for preparing triazole derivatives of formula (I)

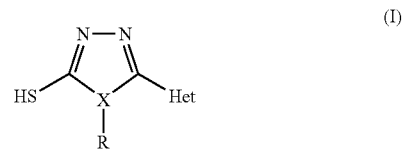

in which

X is nitrogen;

Het is aryl or heteroaryl; each of which may be substituted by 1 to 4 groups J selected from the group consisting of: halogen, $C_1$-$C_6$ alkyl, $C_1$-$C_6$ alkoxy, halo $C_1$-$C_6$ alkyl, $C_2$-$C_6$ alkenyl, $C_2$-$C_6$ alkynyl, halo $C_1$-$C_6$ alkoxy, —C(O)R$_1$, nitro, hydroxy, —NR$_2$R$_3$, and cyano;

R$_1$ is $C_1$-$C_4$ alkyl, —OR$_3$ or —NR$_3$R$_4$;

R$_2$ is hydrogen or $C_1$-$C_6$ alkyl;

R$_3$ is hydrogen or $C_1$-$C_6$ alkyl;

R is methyl;

according to the following Scheme 1:

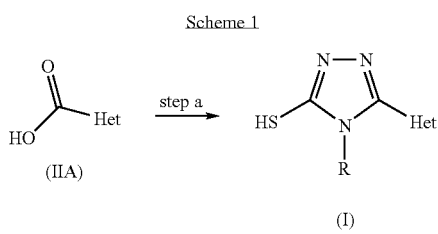

Scheme 1 in which
step a is
(i) a reaction in basic conditions of a compound (IIA) with,
(ii) 4-methyl-3-thiosemicarbazide,
(iii) followed by a treatment with an inorganic base and n-propane phosphonic cyclic anhydride, and
(iv) finally pH adjustement with an inorganic acid to give a compound of formula (I).

2. A process according to claim 1 wherein in the triazole derivative of formula (I), substituted Het is 4-methyl-1,3-oxazol-5-yl.

3. A process according to claim 1 wherein in the triazole derivative of formula (I), substituted Het is 2,4-dimethyl-1,3-thiazol-5-yl.

4. A process according to claim 1 wherein in the triazole derivative of formula (I), substituted Het is 2-methyl-3-pyridinyl.

5. A process according to claim 1 wherein in the triazole derivative of formula (I), unsubstituted Het is 4-pyridazinyl.

6. A process according to claim 1 wherein in the triazole derivative of formula (I), substituted Het is 2,4-dimethyl-1,3-oxazol-5-yl.

* * * * *